(12) United States Patent
Enderby et al.

(10) Patent No.: US 8,970,843 B2
(45) Date of Patent: Mar. 3, 2015

(54) OPTICAL ASSEMBLY AND METHOD FOR DETERMINING ANALYTE CONCENTRATION

(75) Inventors: John Enderby, Bristol (GB); Dawood Parker, Whitland (GB)

(73) Assignee: Melys Diagnostics Ltd, Whitland (GB)

( * ) Notice: Subject to any disclaimer, the term of this patent is extended or adjusted under 35 U.S.C. 154(b) by 0 days.

(21) Appl. No.: 13/808,635

(22) PCT Filed: Jul. 1, 2011

(86) PCT No.: PCT/GB2011/051246
§ 371 (c)(1),
(2), (4) Date: Mar. 7, 2013

(87) PCT Pub. No.: WO2012/004586
PCT Pub. Date: Jan. 12, 2012

(65) Prior Publication Data
US 2013/0155410 A1    Jun. 20, 2013

(30) Foreign Application Priority Data

Jul. 7, 2010 (GB) .................................. 1011459.3
Mar. 25, 2011 (GB) .................................. 1105045.7

(51) Int. Cl.
| G01N 21/55 | (2014.01) |
| A61B 5/145 | (2006.01) |
| A61B 5/1455 | (2006.01) |
| G01N 21/552 | (2014.01) |
| G01N 21/35 | (2014.01) |

(52) U.S. Cl.
CPC ............ *G01N 21/55* (2013.01); *A61B 5/14532* (2013.01); *A61B 5/1455* (2013.01); *G01N 21/552* (2013.01); *G01N 21/35* (2013.01)

USPC .......................................... 356/445; 356/246

(58) Field of Classification Search
USPC .............. 356/246, 445, 36–41; 436/164, 172, 436/805; 250/201.2, 225
See application file for complete search history.

(56) References Cited

U.S. PATENT DOCUMENTS

| 5,028,787 A | 7/1991 | Rosenthal et al. |
| 5,362,966 A | 11/1994 | Rosenthal et al. |
| 5,604,581 A * | 2/1997 | Liu et al. .......................... 356/73 |
| 5,694,930 A | 12/1997 | Pries et al. |
| 6,277,330 B1 * | 8/2001 | Liu et al. ..................... 422/82.05 |
| 6,537,829 B1 * | 3/2003 | Zarling et al. ................ 436/514 |
| 6,567,768 B1 * | 5/2003 | Matos et al. .................. 702/187 |

(Continued)

FOREIGN PATENT DOCUMENTS

| EP | 1464273 | 10/2004 |
| JP | 2005188999 | 7/2005 |

(Continued)

*Primary Examiner* — Sang Nguyen
(74) *Attorney, Agent, or Firm* — Gordon & Jacobson, PC (57) ABSTRACT

An optical assembly and method for the non-invasive determination of a concentration of an analyte in a tissue sample is disclosed. The assembly comprises an optical arrangement comprising a first optical interface for reflecting light incident thereon and a second optical interface for reflecting light incident thereon. The second interface comprises an interface between an optical element of the arrangement and the tissue sample under investigation. The light reflected from the first and second interfaces is arranged to combine to generate an interference pattern characteristic of a difference in phase between light reflected from the first interface with the light reflected from the second interface.

20 Claims, 5 Drawing Sheets

(56) References Cited

U.S. PATENT DOCUMENTS

| | | | |
|---|---|---|---|
| 7,205,518 B2* | 4/2007 | Neuvonen | 250/201.2 |
| 7,417,739 B2* | 8/2008 | Doshoda et al. | 356/445 |
| 8,004,676 B1* | 8/2011 | Prasad et al. | 356/369 |
| 8,673,650 B2* | 3/2014 | Pi | 436/164 |
| 2004/0225206 A1 | 11/2004 | Kouchnir | |
| 2006/0198762 A1 | 9/2006 | Uematsu et al. | |
| 2007/0030475 A1* | 2/2007 | Rowe et al. | 356/71 |
| 2009/0073436 A1* | 3/2009 | Higashi et al. | 356/326 |
| 2010/0073447 A1* | 3/2010 | Jones | 347/99 |

FOREIGN PATENT DOCUMENTS

| | | |
|---|---|---|
| WO | WO91/09312 | 6/1991 |
| WO | WO2009/137122 | 11/2009 |

\* cited by examiner

OPTICAL ASSEMBLY AND METHOD FOR DETERMINING ANALYTE CONCENTRATION

CROSS-REFERENCE TO RELATED APPLICATIONS

This application is a national stage application of PCT/GB2011/051246 filed on Jul. 1, 2011 and claims priority from GB 1011459.3, filed on Jul. 7, 2010 and from GB 1105045.7, filed on Mar. 25, 2011, which are hereby incorporated by reference in their entireties.

BACKGROUND

1. Technical Field

The present invention relates to an optical assembly and method for determining the concentration of an analyte in body fluid and particularly, but not exclusively, to an optical assembly and method for determining the concentration of glucose in body fluid.

2. Related Art

Diabetes mellitus, which is commonly known as diabetes, is the name for a group of chronic diseases that affect the way the body uses food to make the energy necessary for life. Diabetes is primarily a disruption of carbohydrate metabolism with the result that the blood glucose level of a person may vary considerably, from 40 mM (720 mg/dl) to as low as 1 mM (18 mg/dl). In comparison, the blood glucose level of a person without diabetes varies very little, remaining between 4 mM and 8 mM.

In the management of diabetes via insulin, the regular measurement of glucose in the blood is essential in order to ensure a correct administration of insulin. Furthermore, it has been demonstrated that in the long term care of the Type I and Type II diabetic patient, better control of the blood glucose levels can delay, if not prevent, the onset of retinopathy, circulatory problems and other degenerative diseases often associated with diabetes. The majority of diabetes care is self care, and so there is a need for reliable and accurate self-monitoring of blood glucose levels by diabetic patients, since it is essential for the day-to-day care of Type I and Type II diabetes.

Since the late 1970s an increasing number of diabetic patients have been measuring their own blood glucose concentrations using "finger-prick" capillary blood samples. Self blood glucose monitoring is used by Type I diabetics in the home to detect hypoglycemia and hyperglycemia, and therefore to determine the corrective action required, such as taking extra food to raise the blood glucose concentration or extra insulin to lower the blood glucose concentration. These measurements, which are made using low-cost, hand-held blood glucose monitors, also allow the physician to adjust the insulin dosage at appropriate times so as to maintain near normoglycemia. In Type II diabetes, self blood glucose monitoring is used to inform newly diagnosed non-insulin dependent patients about their condition, how to manage it and to monitor themselves with daily or weekly readings as necessary.

These blood glucose monitors use either reflective photometry or an electrochemical method to measure blood glucose concentration. The finger or earlobe of the patient is typically pricked with a sterile lancet and a small sample of blood is placed on the test strip. After analysis, the monitor displays the blood glucose concentration. The main disadvantages of self blood glucose monitoring systems are poor patient acceptance because the technique is painful, only intermittent assessment of diabetic control is possible and readings during the night or when the patient is otherwise occupied are not possible.

The US National Institute of Health has recommended that blood glucose testing should be carried out by Type I diabetic patients at least four times a day, a recommendation that has been endorsed by the American Diabetes Association. This increase in the frequency of blood glucose testing imposes a considerable burden on the diabetic patient, both in financial terms and in terms of pain and discomfort. Thus, there is clearly a need for a better long-term glucose monitoring system that does not involve drawing blood from the patient.

There have been a number of proposals for glucose measurement techniques that do not require blood to be withdrawn from the patient. Many of these methods measure blood glucose concentration using near infrared (NIR) spectroscopy to analyse the glucose concentration in the blood vessels in the skin. For example, U.S. Pat. Nos. 5,028,787 and 5,362,966 describe devices for measuring glucose concentration in a fingertip on passing NIR light (0.6 µm-1.1 µm) light through the finger to the detector, and a similar device that measures the glucose concentration in a vein by shining NIR light on to one part of the vein in the wrist and detecting the light emerging from another part of the vein nearer the elbow. Disadvantages of the use of NIR spectroscopy are that the measurement suffers from interference by other optical absorbers in the tissue and is also dependent on blood flow in the skin. The absorbance peaks of water at these wavelengths are variable in position with temperature such that shifts in water absorbance induced by temperature changes of less than a degree are greater than those induced by a 20 mg/dl variation in glucose concentration.

It has been observed that the concentration of analytes, such as glucose in subcutaneous fluid correlates with the concentration of those analytes in the blood. There have been several techniques developed for measuring the glucose concentration in the tissue; examples include subcutaneous implants containing glucose binding assays, such as that described in W091/09312, in which the degree of binding of the assay component to glucose is indicated by the intensity of fluorescence produced by the assay. This type of device is minimally invasive, as the fluorescence signal is able to be read remotely and so the extraction of a blood sample is avoided, but it does require an invasive operation to install the implant. Therefore, it is apparent that there is a need for an improved method of glucose concentration measurement that may be used regularly by a diabetic patient in the home, which is cheap and simple to use, as well as being accurate and non-invasive in nature.

It is known that an optical waveguide, such as a plate, a prism, or optical fibre may pass light along its length by the process of total internal reflection. In the case of a prism, total internal reflection occurs when the angle of incidence of the light entering the prism exceeds the critical angle, $$\theta c: \theta_c = \sin^{-1}\left(\frac{n_2}{n_1}\right)$$

where $n_2$ is the refractive index of the region outside the prism, and $n_1$ is the refractive index of the prism. At each reflection within the prism, an evanescent wave penetrates a small distance into the surrounding medium. It is therefore possible to obtain an absorption spectrum for the regions of the surrounding medium in contact with the outer surface of the prism, by comparing the light incident upon the prism with that emerging therefrom. This technique is known as attenuated total reflectance (ATR) spectroscopy. The signal-to-noise ratio for the absorption spectrum increases with the number of reflections within the waveguide achieved with evanescent wave interaction with the absorbent before detection of the emerging light. The use of a material with a high refractive index for the prism is therefore preferred, as this minimizes the critical angle $\theta_C$ and thereby maximizes the possible number of reflections back and forth through the waveguide, as the light travels along the waveguide.

Figure 1:
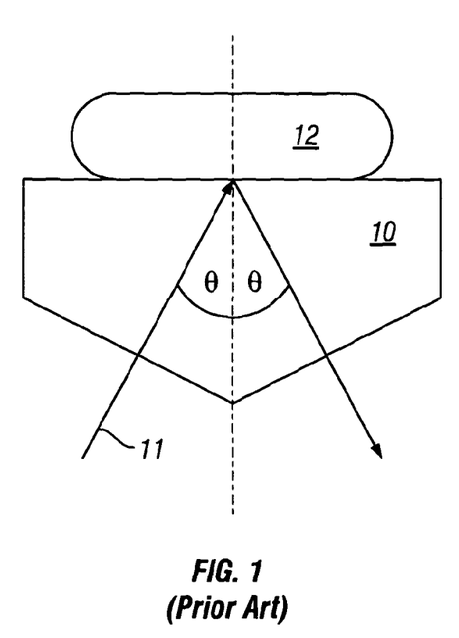
FIG. 1 is a schematic illustration of a conventional ATR element.

A conventional ATR arrangement is illustrated in FIG. 1 of the drawings. The substance to be investigated (e.g. tissue) has a lower refractive index than the ATR element 10 which typically is made of ZnSe or diamond (n=2.4). In the absence of absorbance and for angles of incidence of the incident light 11 greater than the critical angle, total internal reflection occurs. However, when an absorbing material 12 is placed on the surface of the prism 10, an evanescent wave (not shown) is found to penetrate into the material and this evanescent wave is found to attenuate the total internal reflection.

The intensity I of a wave on passing through a distance t in an absorbing material is known to follow Beer's Law, which states:

$$I = I_0 \exp(-\mu t)$$

where $I_0$ is the intensity at the surface of the material and $\mu$ is the linear absorption coefficient, which can be expressed in terms of k, an extinction coefficient by:

$$\mu = 4\pi k/\lambda$$

where $\lambda$ is the wavelength of the light in air.

The behaviour of light in an absorbing material in which both refraction and absorbance occur can be expressed as a complex refractive index given by:

$$\tilde{n} = n + ik$$

where i is the $\sqrt{(-1)}$ and ensures that the effect of k is to attenuate the light. Without i, k would simply add on to n and cause additional refraction. Thus, the optical behaviour of such a medium is completely expressed by $\tilde{n}$, the complex refractive index.

Figure 2:
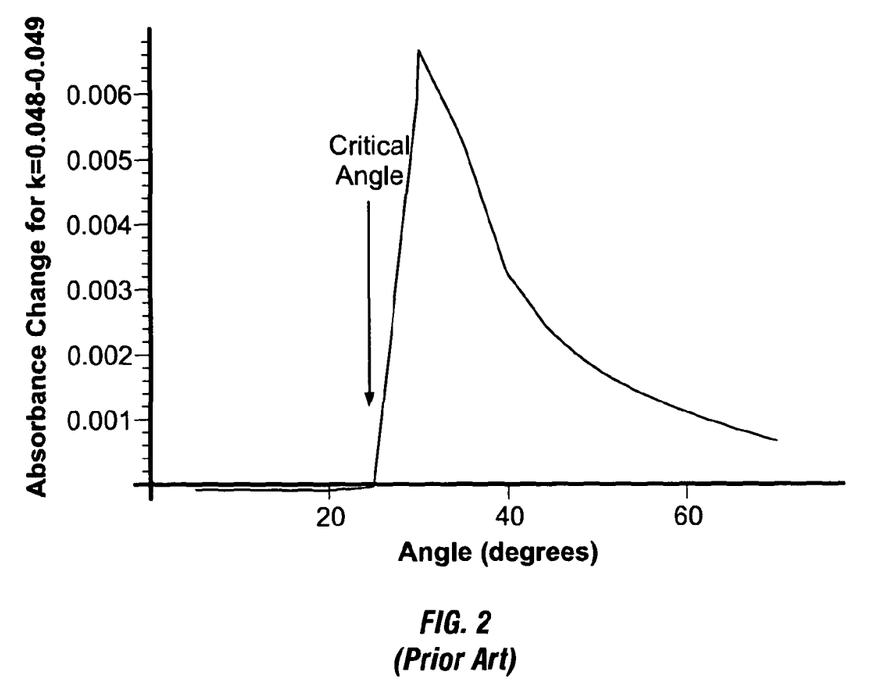
FIG. 2 is a graphical representation of the change in absorption of infra-red light for a change in extinction coefficient of 0.001, as a function of incident angle, illustrating the sensitivity of a conventional ATR element.

Interstitial fluid, namely the fluid disposed between cells within a tissue sample is known to have a glucose concentration that correlates with the blood glucose concentration. Referring to FIG. 2 of the drawings, the maximum sensitivity to analyte absorbance within a tissue sample occurs at or just greater than the critical angle. If the angle is reduced, ATR becomes insensitive to the analyte, i.e. no measurement of analyte concentration is possible.

Figure 3:
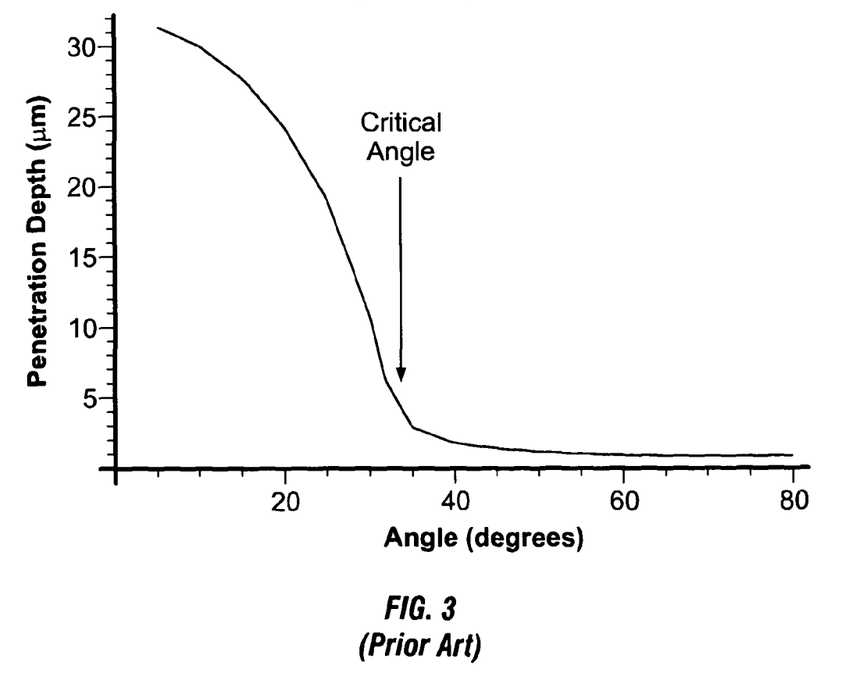
FIG. 3 is a graphical representation of the penetration depth of infra-red light within a tissue sample as a function of incident angle using a conventional ATR element.

Referring to FIG. 3 of the drawings, the penetration depth $\delta$ of the wave into the absorbing material, namely the depth to which an electric field associated with the evanescent wave decays to 1/e (approx 37%) of the value at the surface of the material, reduces significantly as the incident angle increases to the critical angle and beyond. In order to interrogate the interstitial fluid in the epidermis optically it is therefore necessary to penetrate beyond the stratum corneum.

Fingertips typically have stratum corneum thickness of up to 400 μm. However, at the critical angle the value of $\delta$ is typically only 3 μm so that the effective penetration depth for most subjects is insufficient for making a measurement of analyte concentration. Accordingly, it is only by going to reduced angles that the effective depth is significantly increased; however, as stated above, there is no sensitivity to analyte concentration at angles less than the critical angle. It is for these reasons that conventional ATR cannot measure glucose and other analyte concentration in the majority of subjects non-invasively.

SUMMARY

We have now devised an optical assembly and method for determining the concentration of an analyte in body fluid.

According to a first aspect of the present invention there is provided an optical assembly for the non-invasive determination of a concentration of an analyte in a tissue sample, the assembly comprising an optical arrangement comprising a first optical interface for reflecting light incident thereon and a second optical interface for reflecting light incident thereon, the light reflected from the first and second interfaces being arranged to combine to generate an interference pattern characteristic of a difference in phase between light reflected from the first interface with the light reflected from the second interface, wherein the second interface comprises an interface between an optical element of the arrangement and the tissue sample.

The light reflected from the second interface will comprise a phase shift with respect to the light reflected from the first interface and this phase shift is dependent on the extinction coefficient k of the tissue sample which relates to the glucose concentration in the interstitial fluid of the tissue, for example.

Preferably, the optical assembly further comprises a light source, such as a broadband laser source, for launching light upon the first and second interface. The light source may comprise a quantum cascade laser and is arranged to generate light having a wavelength range in the infra-red region of the electromagnetic spectrum.

The assembly preferably further comprises monitoring means for monitoring the interference between the light from the first and second interface. The monitoring means which may include an IR detector or spectrum analyser is arranged to analyse the interference pattern created by the light reflected from the first and second interfaces.

Preferably, the assembly further comprises processing means for processing the interference to determine the concentration of the analyte in the tissue sample.

According to a first embodiment of the invention, the optical arrangement preferably comprises a first optical element and a second optical element, the first and second elements being coupled together to form the first interface therebetween, the second element being arranged to contact a surface portion of the tissue to form a second interface, wherein, the second element comprises a refractive index which is greater than a refractive index of the first element and the surface portion of the tissue.

The provision of a second element having a larger refractive index than the first element and the tissue sample, ensures that light which is incident upon the second interface is incident at an angle less than the critical angle for total internal reflection in the second element, and therefore penetrates beyond the stratum corneum to the required depth for absorption by the analyte in the tissue sample.

The light is preferably launched upon the first interface at an angle such that the light refracted into the second element becomes incident upon the second interface at an angle less than the critical angle for total internal reflection of the light within the second element.

Preferably, the second element is thin compared with the first element, and preferably comprises a film disposed upon the first element. The thickness of the second element is preferably dependent on the wavelength of the incident light.

The first element preferably comprises calcium fluoride and second element preferably comprises parylene.

According to a second embodiment of the present invention, the optical arrangement preferably comprises an interferometer comprising a first and second element for reflecting light incident thereon, and a routing device which is arranged to route a first component of the light incident thereon toward the first element and a second component of the light incident thereon toward the second element, the first and second elements comprising a front and rear reflecting surface, wherein the front surface of each element comprises an anti-reflection coating for minimising any reflection of light off the front surface of the respective element and the rear surface of the second element is arranged to contact the tissue sample.

The first interface of the second embodiment preferably comprises an interface of the rear surface of the first element with air, and the second interface comprises an interface between the rear surface of the second element with the tissue sample.

Preferably, the interference pattern is characteristic of a difference in phase of the light incident on the second element with the light reflected off the second element.

The first and second elements of the first and second embodiments are preferably substantially transmissive for wavelengths in the infra-red region of the electromagnetic spectrum.

Preferably, the analyte comprises glucose.

According to a second aspect of the present invention there is provided a method for the non-invasive determination of the concentration of an analyte in a tissue sample, the method comprising the steps of:
arranging the second element of the optical arrangement according to the first or second embodiment in contact with the tissue sample;
launching light upon the first and second interfaces;
monitoring the interference between the light which becomes reflected off the first and second interfaces; and,
processing the monitored light to determine the concentration of an analyte in the body fluid.

Preferably, the method comprises the use of attenuated total reflectance.

In accordance with a third aspect of the present invention there is provided a glucose monitor for the non-invasive determination of the concentration of glucose in a tissue sample, the monitor comprising an optical assembly according to the first aspect, a light source for launching light upon the first and second interfaces and monitoring means for monitoring the light which becomes reflected off the first and second interfaces.

Embodiments of the present invention will now be described by way of example only and with reference to the accompanying drawings.

DETAILED DESCRIPTION OF THE EMBODIMENTS

Figure 4:
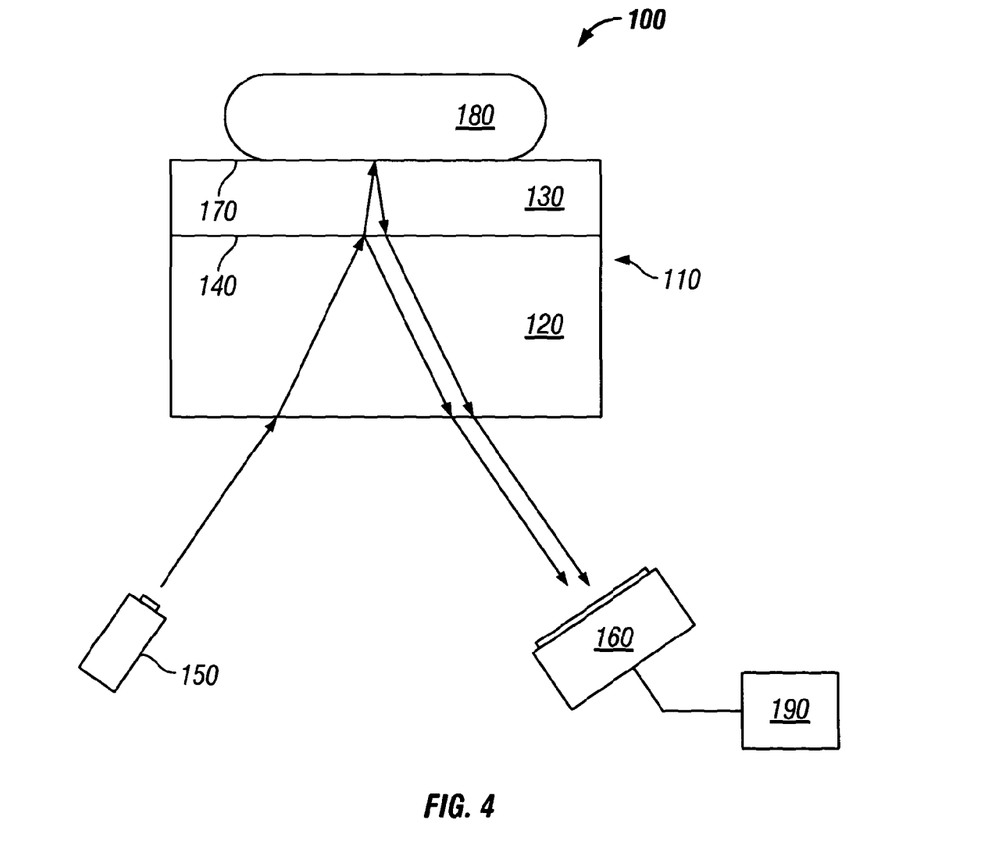
FIG. 4 is a schematic illustration of an optical assembly according to a first embodiment of the present invention.

Referring to FIG. 4 of the drawings, there is illustrated an optical assembly 100a according to a first embodiment of the present invention comprising an optical arrangement 110a, for the non-invasive determination of the concentration of an analyte, such as glucose, in a tissue sample, such as body fluid.

The optical arrangement 110a illustrated comprises a substantially rectangular cuboid shape however, it is to be appreciated that other shapes may also be used. The arrangement comprises a first, relatively thick layer 120 of calcium fluoride, for example and a second, relatively thin layer 130 of parylene for example, disposed upon the first layer 120 and coupled thereto to form an interface 140 between the first and second layers 120, 130. The first and second layers 120, 130 are substantially transmissive to light in the infra-red region of the spectrum, namely in the wavelength range 1-10 μm, such that light in this wavelength range can pass through the first and second layers 120, 130.

The assembly 100a further comprises a collimated light source 150, such as an incandescent light source or quantum cascade laser for producing a broad range of wavelengths over the infra-red region of the spectrum, and monitoring means 160 such as an infra-red detector and/or spectrum analyzer for monitoring the light which becomes reflected out from the arrangement 110a.

It has been shown that the stratum corneum (not shown) comprises a thickness of approximately 400 μm on the finger tips (not shown), however a recent study has found that the stratum corneum (not shown) on the volar forearm (not shown) rarely exceeds 18 μm. Accordingly, during use the optical arrangement 110a is placed upon the volar forearm (not shown) with the second layer 130 in contact therewith and infra-red light is directed upon the interface 140 between the first and second layer 120, 130, from the first layer 120. The refractive index of the second layer 130 is chosen to be greater than that of the first layer 120 and the portion of the forearm (not shown) in contact with the second layer 130, and the light is incident upon the interface 140 at an angle which ensures that the light becomes refracted into the second layer 130 at an angle less than the critical angle for total internal reflection within the second layer 130.

The light which passes into the second layer 130 is arranged to subsequently strike the interface 170 between the second layer 130 and the tissue 180 and partially penetrate into the tissue 180. However, due to the presence of the extinction coefficient k, the light will decay as it propagates into the forearm (not shown). The light will also partially reflect from the interface 170 between the second layer 130 and the tissue 180 and pass back toward the interface 140 between the first and second layers 120, 130, whereupon a similar partial reflection and transmission will occur.

The light which reflects from the optical arrangement 110a will therefore comprise a component reflected from the interface 140 between the first and second layers 120, 130 and a component from the interface 170 between the second layer 130 and the tissue 180. The light reflected from the interface 140 between the layers 120, 130 will have constant amplitude and phase whereas the light reflected from the interface 170 with the tissue 180 will comprise a phase shift characteristic of the extinction coefficient k of the tissue sample 180. This relative phase shift between the reflected components will manifest as an interference pattern which is monitored using the detector and/or spectrum analyser 160 and subsequently processed using a processor 190 to determine glucose concentration in the interstitial fluid.

Interstitial fluid (not shown) typically consists of water, salts, glucose, lactate, urea and triglycerides, and water has been shown to comprise a substantially uniform absorption in the mid-IR range (6-10 µm, wave number 1600-1000 cm$^{-1}$). The method according to an embodiment of the present invention compensates for the effects of the hydration levels of the skin, both directly in terms of the water absorbance and indirectly in terms of the effect of hydration on the absorbance of the stratum corneum (not shown) and other analytes present in the interstitial fluid (not shown). Salts do not absorb in this wavelength range whereas glucose, lactate, urea and triglycerides all have strong absorbance. Each of these analytes has characteristic IR spectra, one example of which is the absorption spectrum for glucose, as illustrated in FIG. 5 of the drawings.

Figure 5:
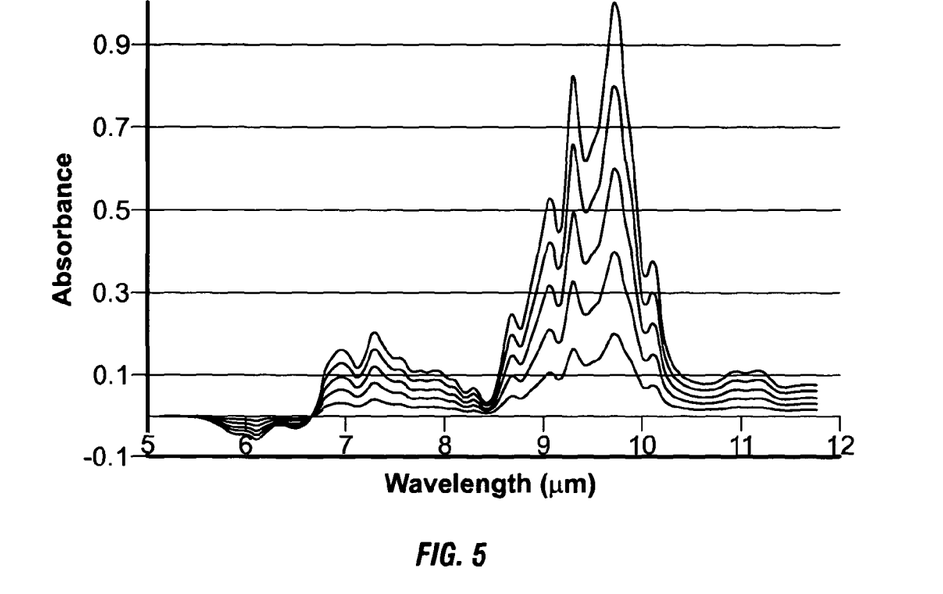
FIG. 5 is a graphical representation of a typical absorption spectrum of glucose in water, for various glucose concentrations.

The spectrum illustrated in FIG. 5 of the drawings is characteristic of glucose in water. However, when measurements are made in tissue, this glucose spectrum is modified by the presence of other analytes, such as lactate, urea, and triglycerides. It is therefore necessary to extract the glucose signal from the contribution from these analytes. This is achieved using a least squares method and requires the use of a broad band IR source 150 and detector 160 designed to cover 3 µm (for water) and 5-10 µm (for glucose), such as an incandescent emitter or a broad band quantum cascade laser. The indirect effect of hydration on the absorbance of tissue referred to above, is compensated by the observation that there is equality of absorbance, which is independent of the degree of hydration for tissue at 8.5 µm (no glucose band) and 9.6 µm (strong glucose band).

Figure 6:
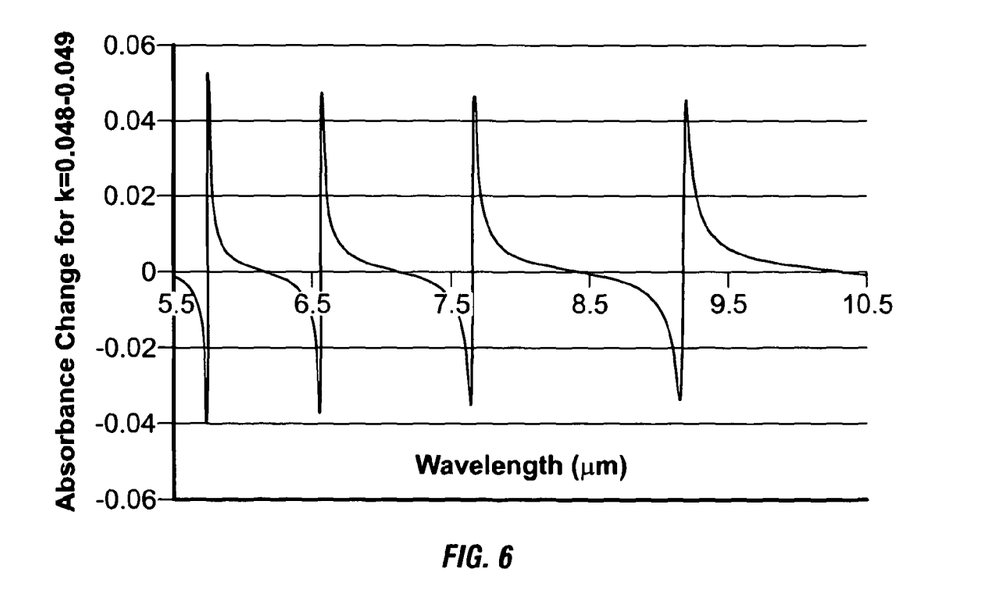
FIG. 6 is a graphical representation of the change in absorption of infra-red light for a change in the extinction coefficient of 0.001, as a function of incident wavelength, illustrating the sensitivity of the optical element of FIG. 4; and, FIG. 7 is a schematic illustration of an optical assembly according to a second embodiment of the present invention.

It has been shown that if the glucose concentration in the interstitial fluid (not shown) changes by 1-2 mM, the extinction coefficient, k, will change by approximately 0.001. It is therefore essential that the absorbance can be measured for such a small change in glucose concentration. Referring to FIG. 6 of the drawings there is illustrated a graphical representation of the change in absorbance of unpolarised infra-red light for a change in the extinction coefficient of 0.001, as a function of incident wavelength. It is evident from FIG. 6 that at a wavelength of 9.6 µm which represents a significant peak in the glucose absorption spectrum (FIG. 5), an increase in absorbance of 0.03 is predicted, which can be detected and measured using current infra-red technology. Similarly, at 7.7 µm, a wavelength where there is significant glucose absorbance, an increase of 0.025 is predicted. It has been further realised however, that the difference between the absorbance change associated with parallel and transverse polarisation states provides for an increased sensitivity for a similar change in extinction coefficient.

In order to calibrate the optical arrangement 110a, water is first placed on the second layer 130 of the arrangement 110a and the absorbance measured and recorded at 3 µm and in the range 5-10 µm. Standard solutions of glucose, lactate and urea are subsequently and separately placed on the second layer 130 of the arrangement 110a and the absorbance measured and recorded in the range 5-10 µm. This calibration data is then stored for subsequent retrieval during use. If necessary, the calibration data for water and glucose can be repeated by the end user.

In order to calibrate the arrangement 110a for a particular user, an initial conventional determination of blood glucose will be made so that the subject specific absorbance due to tissue within the stratum corneum (not shown) and epidermis (not shown) can be determined. This is denoted A(tissue). The absorbance values which are subsequently measured, namely A(total), A(lactate at 5.3 µm), A(urea at 5.6 µm), A(water at 3 µm) and A(glucose from blood test) can then be used to A(tissue), using the relation:

$$A(\text{tissue})=A(\text{total})-A(\text{water})-A(\text{glucose})-A(\text{lactate})-A(\text{urea})$$

The total absorbance measured during the subsequent non-invasive determination of blood glucose levels can then be recorded and a least squares analysis software program is used to extract the glucose concentration, since all other sources of absorbance will have been accounted for.

Figure 7:
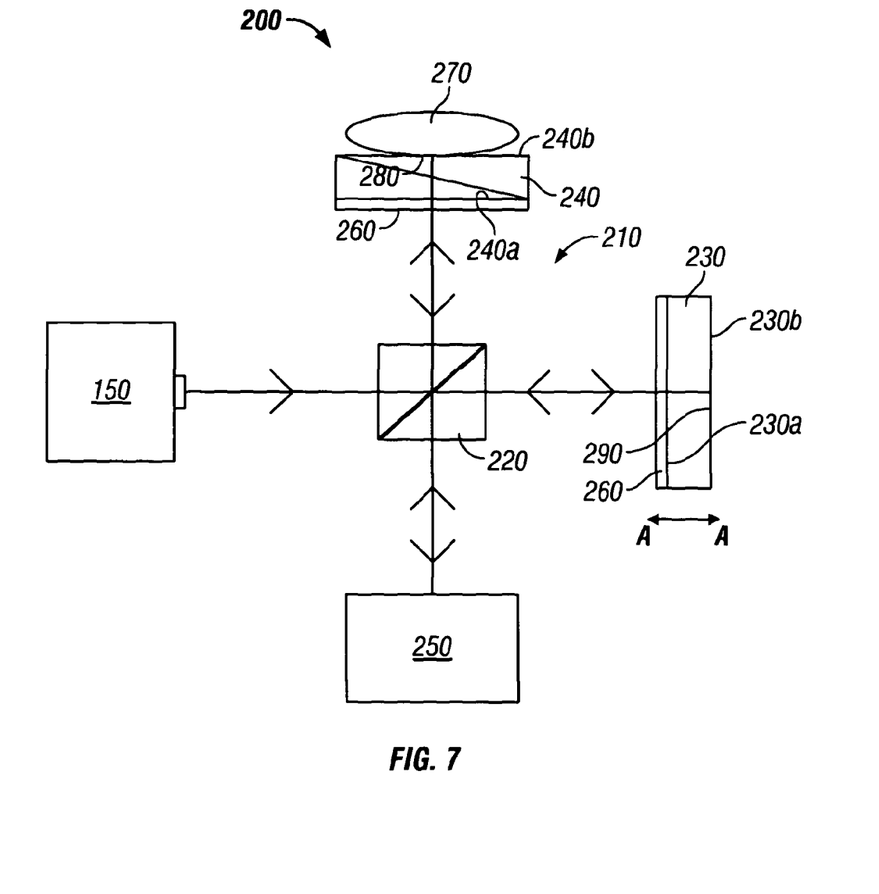

Referring to FIG. 7 of the drawings, there is illustrated an optical assembly 200 according to a second embodiment of the present invention for the non-invasive determination of the concentration of an analyte, such as glucose, in a tissue sample. The assembly 200 comprises an optical arrangement 210 and a broadband light source 150, such as a broadband laser which is arranged to launch laser light having a wavelength characteristic of infra-red wavelengths. The optical arrangement 210 comprises an interferometer comprising a beam splitter 220 which is arranged to partially reflect and partially transmit incident laser light toward a first and second reflector element 230, 240, respectively.

The reflector elements 230, 240 may be formed of zinc selenide and comprise substantially planar element. The elements 230, 240 are orientated to reflect the light incident thereon back toward the beam splitter 220, substantially along the same path as the incident light. In this respect, the elements 230, 240 are orientated substantially perpendicular to the direction of the light incident thereon. The light returned to the beam splitter 220 from the elements 230, 240 is then recombined and directed toward a detector 250, such as a spectrum analyzer.

The light reflected from the elements 230, 240 will comprise a component reflected from the front 230a, 240a and rear surfaces 230b, 240b thereof, which due to the optical path length associated with the thickness of the respective element 230, 240, will give rise to a phase shift between the component reflected off the front surface 230a, 240a and the component reflected off the rear surface 230b, 240b, and thus interference from each reflector 230, 240. To minimise this interference, the front surface 230a, 240a of each reflector is coated with an anti-reflection coating 260 to minimise the reflection of the light from the front surfaces 230a, 240a. The resulting interference from the combination of the light from each reflector 230, 240 will therefore be due to the difference in optical path length arising from the separation of the rear surface 230b, 240b of the elements 230, 240 from the beam splitter 220.

One of the elements 230, 240 of the interferometer is arranged to move with respect to the beam splitter 220 along the direction indicated by arrow A-A, to adjust the separation therebetween to tune the optical path length difference to correspond with an integral number of wavelengths, and thus to ensure that the light recombines at the beam splitter 220 in phase to create a strong optical signal.

Once the interferometer has been suitably tuned, a sample 270 is then placed in contact with the rear surface 240b of the fixed element such that the light which is incident on the rear surface 240b illuminates the sample 270. The light which is incident on the sample 270 will partially transmit into the sample 270 and become absorbed therein due to the extinction coefficient. However, since the light is incident upon the sample/element interface 280 in a direction which is substantially normal to the interface, then this will ensure maximum penetration into the sample 270, so that the light becomes absorbed by the analytes within the sample 270.

The light will also partially reflect at the sample/element interface 280 and will undergo a phase shift characteristic of the absorbance of the light in the sample 270. The light which is incident upon the rear surface 230b of the first element 230, will encounter an interface 290 with air and will therefor undergo no phase change. The absorbance has been shown above to be proportional to the extinction coefficient of the light in the sample 270. Accordingly, the resulting interference of the light from the first and second reflectors 230, 240 will be characteristic of the phase shift of the light at the sample/element interface 280 and thus the extinction coefficient, which has been shown above to be related to the glucose concentration in body fluid, for example.

From the foregoing therefore, it is evident that the optical element, assembly and method according to the above described embodiments of the present invention provides for a simple yet effective means of determining glucose concentration in body fluid non-invasively.

While the preferred embodiments of the invention have been shown and described, it will be understood by those skilled in the art that changes of modifications may be made thereto without departing from the true spirit and scope of the invention.

The invention claimed is:

1. An optical assembly for the non-invasive determination of a concentration of an analyte in a tissue sample, the assembly comprising:
    an optical arrangement comprising a first optical interface for reflecting light incident thereon and a second optical interface for reflecting light incident thereon, the light reflected from the first and second interfaces being arranged to combine to generate an interference pattern characteristic of a difference in phase between light reflected from the first interface with the light reflected from the second interface, wherein the second interface comprises an interface between an optical element of the arrangement and the tissue sample;
    wherein the optical arrangement comprises a first optical element and a second optical element, the first and second elements being coupled together to form the first interface therebetween, the second element being arranged to contact a surface portion of the tissue to form the second interface, wherein the second element comprises a refractive index which is greater than a refractive index of the first element and the surface portion of the tissue.

2. An optical assembly according to claim 1, further comprising:
    a light source for launching light upon the first and second interface.

3. An optical assembly according to claim 2, wherein:
    the light source comprises a laser source.

4. An optical assembly according to claim 1, further comprising:
    a monitor for monitoring the interference between the light from the first and second interface.

5. An optical assembly according to claim 1, further comprising:
    a processor for processing the interference to determine the concentration of the analyte in the tissue sample.

6. An optical assembly according to claim 1, wherein:
    the light is launched upon the first interface at an angle such that the light refracted into the second element becomes incident upon the second interface at an angle less than the critical angle for total internal reflection of the light within the second element.

7. An optical assembly according to claim 1, wherein:
    the second element is thin compared with the first element.

8. An optical assembly according to claim 1, wherein:
    the second element comprises a film disposed upon the first element.

9. An optical assembly according to claim 1, wherein:
    the thickness of the second element is dependent on the wavelength of the incident light.

10. An optical assembly according to claim 1, wherein:
    the first element comprises calcium fluoride and the second portion comprises parylene.

11. An optical assembly according to claim 1, wherein:
    said optical arrangement further comprises a routing device which is arranged to route a first component of the light incident thereon toward the first element and a second component of the light incident thereon toward the second element, the first and second elements comprising a front and rear reflecting surface, wherein the front surface of each element comprises an anti-reflection coating for minimizing any reflection of light off the front surface of the respective element and the rear surface of the second element is arranged to contact the tissue sample.

12. An optical assembly according to claim 11, wherein:
    the first interface comprises an interface of the rear surface of the first element with air, and the second interface comprises an interface between the rear surface of the second element with the tissue sample.

13. An optical assembly according to claim 11, wherein:
    the interference pattern is characteristic of a difference in phase of the light incident on the second element with the light reflected off the second element.

14. An optical assembly according to claim 1, wherein:
    the analyte comprises glucose.

15. An optical assembly according to claim 1, wherein: the first and second elements are substantially transmissive for wavelengths in the infra-red region of the electromagnetic spectrum.

16. A method for the non-invasive determination of the concentration of an analyte in a tissue sample, the method comprising:
    arranging the second element of the optical arrangement according to claim 1 in contact with the tissue sample;
    launching light upon the first and second interfaces of the optical arrangement;
    monitoring the interference between the light which becomes reflected off the first and second interfaces; and,
    configuring a processor to process the monitored light in order to determine the concentration of an analyte in the body fluid.

17. A method according to claim 16, wherein:
    the optical arrangement utilizes attenuated total reflectance.

18. A glucose monitor for the non-invasive determination of the concentration of glucose in body fluid, the monitor comprising:
    an optical assembly according to claim 1;

a light source for launching light upon the first and second interfaces; and a monitor for monitoring the light which becomes reflected off the first and second interfaces.

19. An optical assembly according to claim 1, wherein: light incident on the second surface penetrates into the tissue sample and reflects from the second interface while undergoing a phase change characteristic of the extinction coefficient of the tissue sample.

20. An optical assembly according to claim 19, wherein: relative phase shift between the light reflected at the first interface and the light reflected as the second interface produces an interference pattern that is processed to in order to determine concentration of the analyte in the tissue sample.

\* \* \* \* \*